United States Patent [19]
Wright

[11] Patent Number: 5,868,776
[45] Date of Patent: Feb. 9, 1999

[54] OVERLAY DUAL BALLOON CATHETER AND METHOD FOR USE THEREOF

[75] Inventor: Larry A. Wright, St. Petersburg, Fla.

[73] Assignee: Ideas For Medicine, Inc., St. Petersburg, Fla.

[21] Appl. No.: 707,186

[22] Filed: Sep. 3, 1996

[51] Int. Cl.⁶ .................................................. A61M 29/00
[52] U.S. Cl. ............................................. 606/194; 604/96
[58] Field of Search ........................... 606/191, 192–196; 604/96, 104

[56] References Cited

U.S. PATENT DOCUMENTS

| | | |
|---|---|---|
| 5,195,969 | 3/1993 | Wang et al. . |
| 5,295,962 | 3/1994 | Crocker et al. . |
| 5,304,132 | 4/1994 | Jang . |
| 5,308,323 | 5/1994 | Sogawa et al. . |
| 5,320,604 | 6/1994 | Walker et al. . |

*Primary Examiner*—Michael Powell Buiz
*Assistant Examiner*—Nancy Mulcare
*Attorney, Agent, or Firm*—William A. Birdwell & Associates

[57] ABSTRACT

An overlay dual balloon catheter. Two balloons composed of differing materials are employed, the balloons being disposed so as to overlap one another but not being bonded to one another, so that adjacent surfaces of the two balloons are permitted to move relative to one another, to provide improved surface and structural characteristics in a balloon unit. Preferably, an outer balloon, disposed on the exterior of the catheter is composed of latex, silicone, or a thermoplastic elastomer while an inner balloon, disposed underneath the first balloon is composed of a material employed in existing angioplasty balloons such as polyester or polyurethane. The overlay dual balloon catheter may be used in angioplasty, embolectomy and thrombectomy.

29 Claims, 6 Drawing Sheets

OVERLAY DUAL BALLOON CATHETER AND METHOD FOR USE THEREOF

BACKGROUND OF THE INVENTION

This invention relates to balloon catheters and relates particularly to the employment of multiple materials and overlay construction in a catheter balloon unit for both improving and tailoring of the characteristics of the balloon unit.

Balloons in a balloon catheter are employed in a patient's body canal, commonly a blood vessel, primarily for three purposes: occlusion, distension (e.g., angioplasty) and vessel cleaning or removal of clots and foreign substances (e.g., embolectomy, thrombectomy). For serving the first purpose, the balloon must be supple enough when inflated to conform completely to the interior surface of the body canal and the surface must have an adequate frictional characteristic to hold the balloon in place. For the second purpose, the balloon must be stiff enough to inflate symmetrically even while being influenced by asymmetric forces. And for the third purpose, the surface must be tear resistant, with good tensile properties, and again must have an appropriate frictional characteristic. Especially because both surface and structural characteristics, such as strength, rigidity and tear resistance, are important, a balloon comprising a single material generally requires the acceptance of trade-offs in the characteristics of the material. Even in view of this, there appear to be few attempts to employ multiple materials in a balloon in an effort to minimize trade-offs so as to optimize desirable characteristics. One reference, Wang, et al., U.S. Pat. No. 5,195,969 ("Wang"), proposes "CO-EXTRUDED MEDICAL BALLOONS AND CATHETER USING SUCH BALLOONS" comprising a multi-layered balloon including a base structural layer of relatively thick ethylenic polymeric material and a second layer co-extruded and apparently bonded co-extensively with the base layer, the second layer preferably being a polyolefin such as polyethylene.

However, even a multiple material balloon such as that proposed by Wang has disadvantages. For example, it is often desired that the balloon present a non-convoluted surface to the interior of the body canal when the balloon is deflated, to facilitate passing the balloon therethrough. If a strong base material is co-extruded with, for example, a soft surface material, the base material is often insufficiently elastic for relaxing to a smooth surface configuration when the balloon is deflated. Moreover, deflation and complete collapse of the balloon, which is resisted by employing a stiff, strong base material, is not aided appreciably by employing a soft co-extruded surface layer.

Accordingly, there is a need for a novel balloon catheter and method for use thereof that employs multiple materials and provides an overlaid construction for optimizing both the surface and structural characteristics of a balloon unit.

SUMMARY OF THE INVENTION

The overlay dual balloon catheter and method for use thereof of the present invention solves the aforementioned problems and meets the aforementioned need by employing two balloons composed of differing materials, the balloons being disposed so as to overlap one another and having working portions thereof not being bonded to one another, so that the working portions of the two balloons are permitted to move relative to one another, to provide improved surface and structural characteristics in a balloon unit. Preferably, an outer balloon, disposed on the exterior of the catheter is composed of latex, silicone, or a thermoplastic elastomer while an inner balloon, disposed underneath the first balloon is composed of a material employed in existing angioplasty balloons such as polyester, polyurethane or polyethylene.

Therefore, it is a principal object of the present invention to provide a novel and improved balloon catheter and method for use thereof.

It is another object of the present invention to provide such a balloon catheter employing overlaid balloons.

It is a further object of the present invention to provide such a catheter that optimizes both the surface and structural characteristics of the balloon unit.

It is yet another object of the present invention to provide such a catheter that provides for movement between adjacent surfaces of the two balloons.

The foregoing and other objects, features and advantages of the present invention will be more readily understood upon consideration of the following detailed description of the invention, taken in conjunction with the following drawings.

DETAILED DESCRIPTION OF A PREFERRED EMBODIMENT

Figure 1:
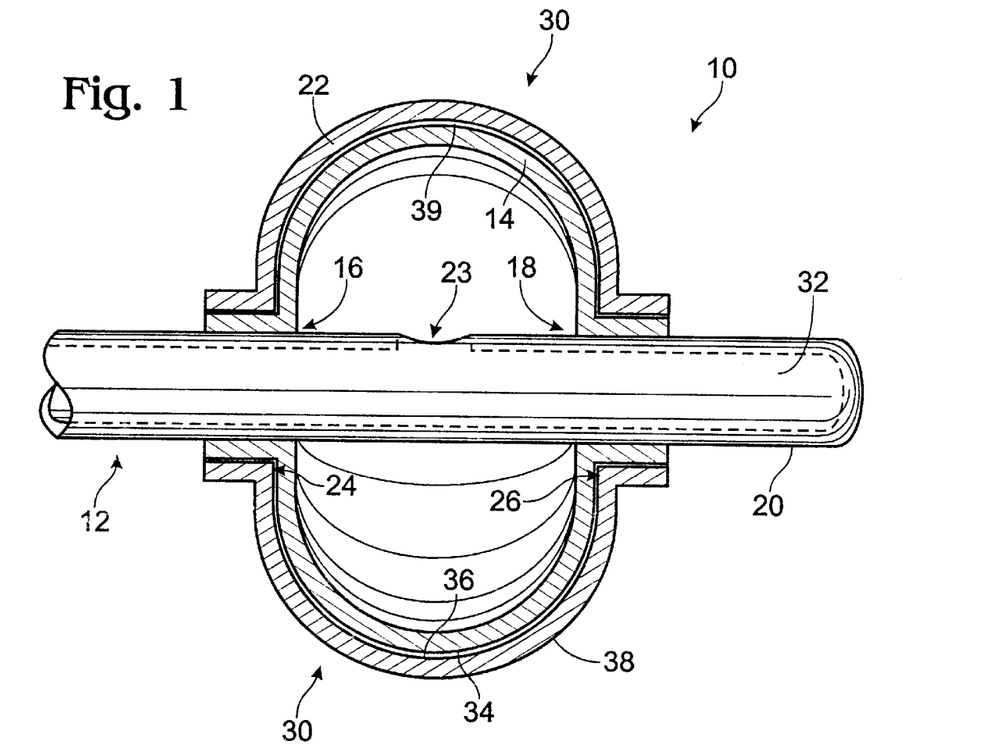
FIG. 1 is a partially cut-away side elevation of a balloon catheter having a balloon unit according to the present invention in combination with a catheter, shown in an inflated condition.
Figure 2:
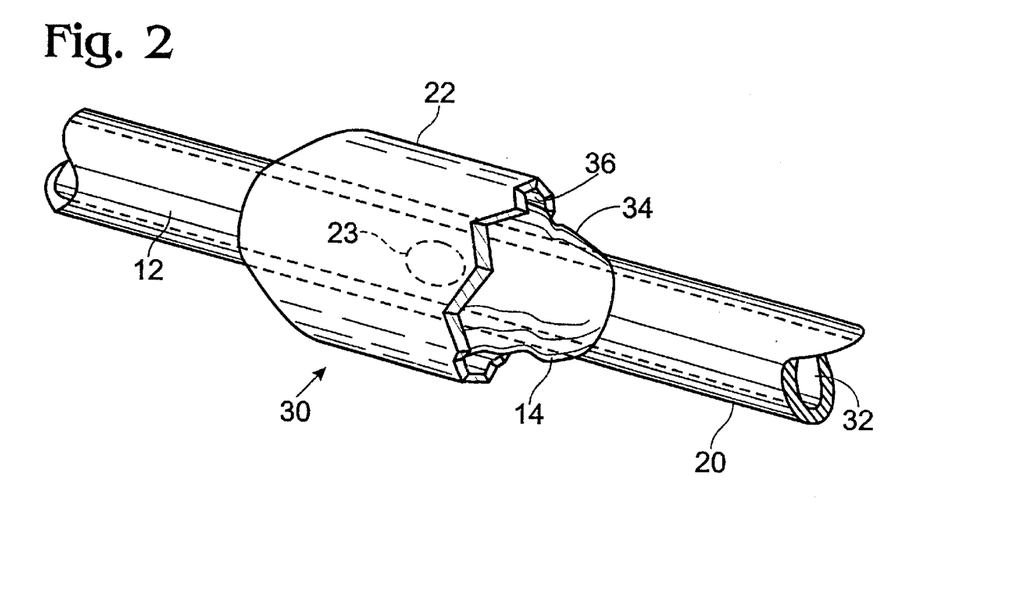
FIG. 2 is a partially cut-away pictorial view of the balloon catheter of FIG. 1, shown in a partially inflated condition.
Figure 3A:
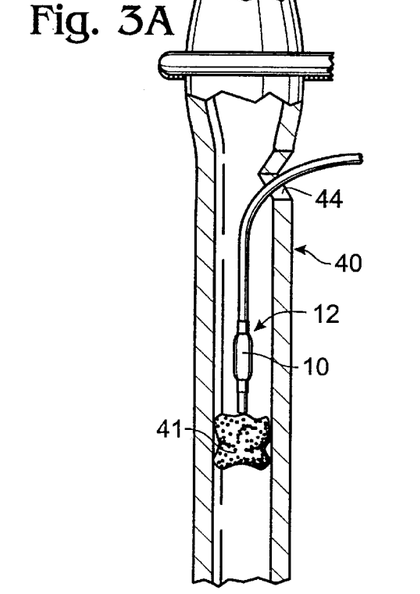
FIG. 3A is a cross-section of a blood vessel and a balloon catheter according to the present invention being fed toward an obstruction.
Figure 3B:
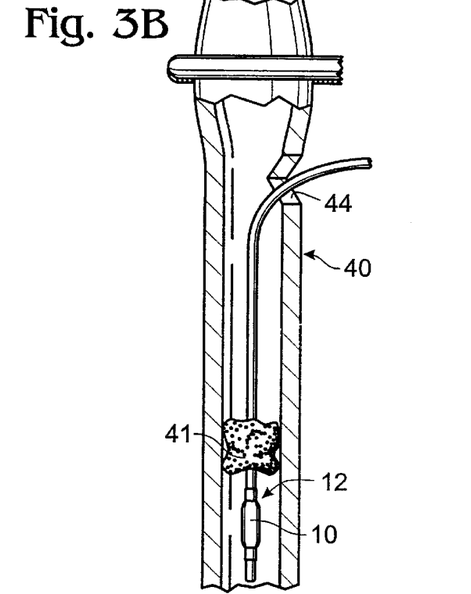
FIG. 3B is a cross-section of the blood vessel and balloon catheter of FIG. 3A having been fed through the obstruction.
Figure 3C:
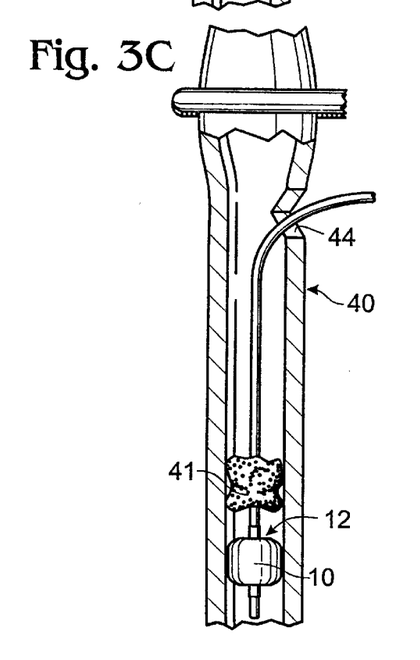
FIG. 3C is a cross-section of the blood vessel and balloon catheter of FIG. 3A with the balloon unit being inflated.
Figure 3D:
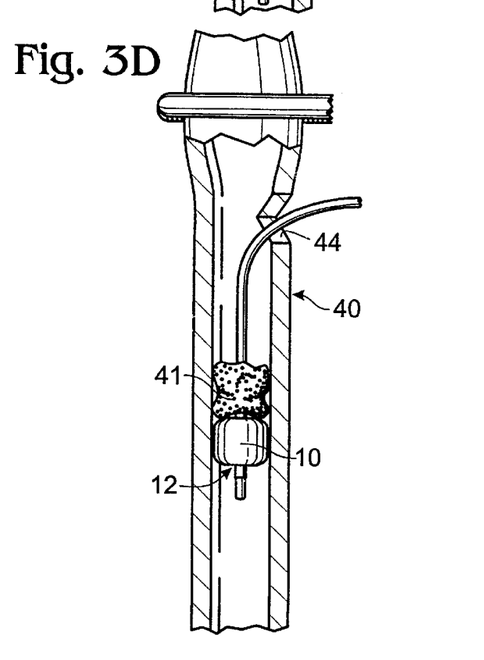
FIG. 3D is a cross-section of the blood vessel and balloon catheter of FIG. 3A with the catheter and the obstruction being withdrawn from the blood vessel.
Figure 4A:
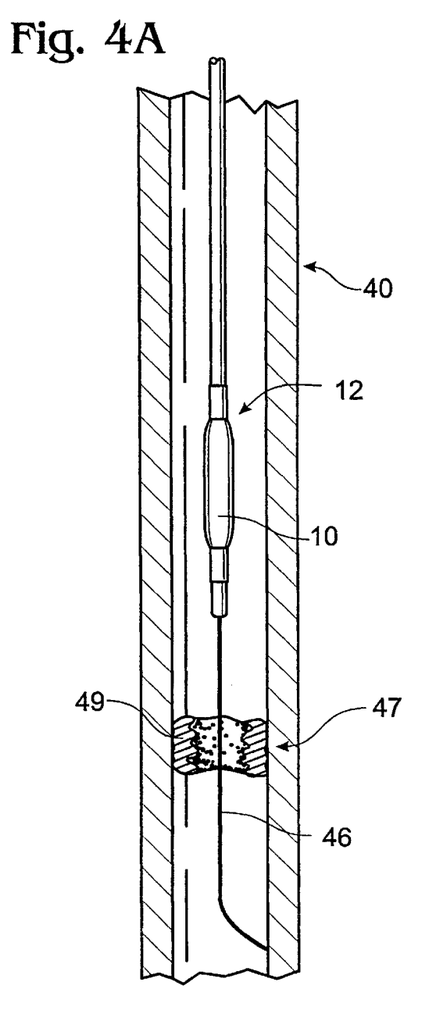
FIG. 4A is a cross-section of a blood vessel and a balloon catheter according to the present invention being fed along a guidewire toward an area of stenosis in the blood vessel.
Figure 4B:
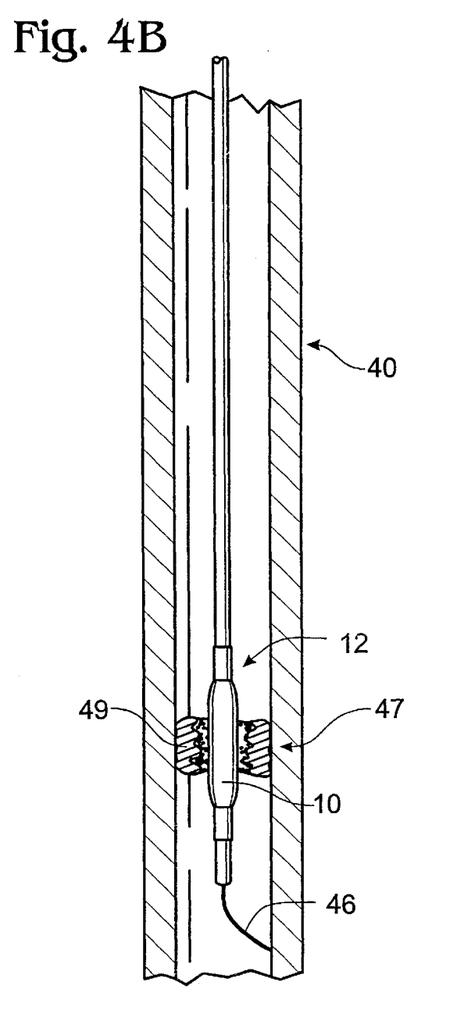
FIG. 4B is a cross-section of the blood vessel and balloon catheter of FIG. 4A with the balloon unit being placed at the area of stenosis.
Figure 4C:
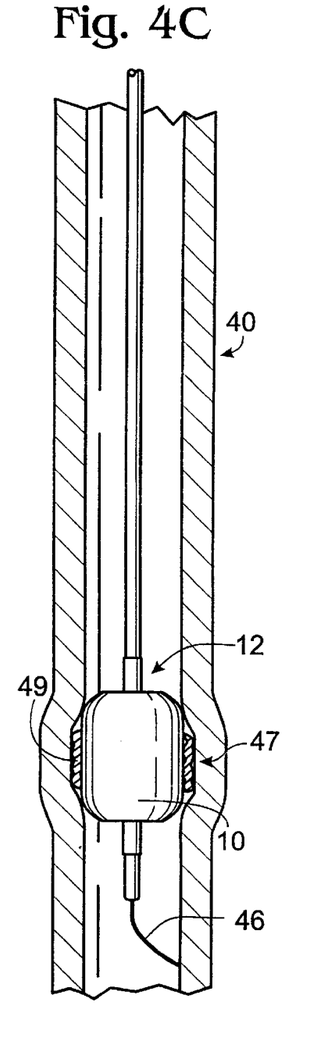
FIG. 4C is a cross-section of the blood vessel and balloon catheter of FIG. 4A with the balloon unit being inflated against stenotic material at the area of stenosis to relieve the area of stenosis.
Figure 4D:
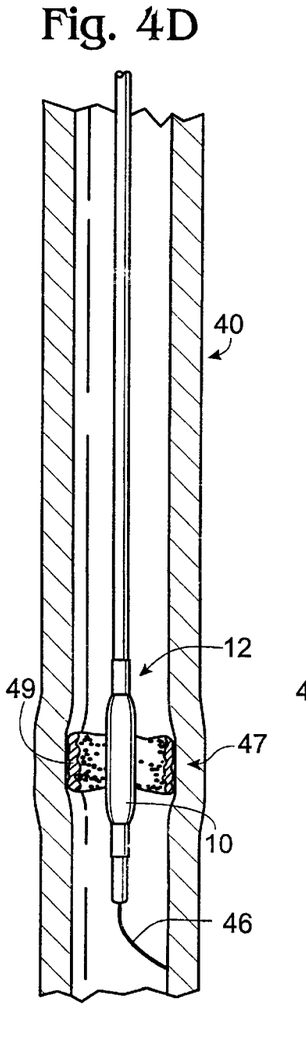
FIG. 4D is a cross-section of the blood vessel and balloon catheter of FIG. 4A with the balloon unit being deflated in preparation for withdrawal.
Figure 4E:
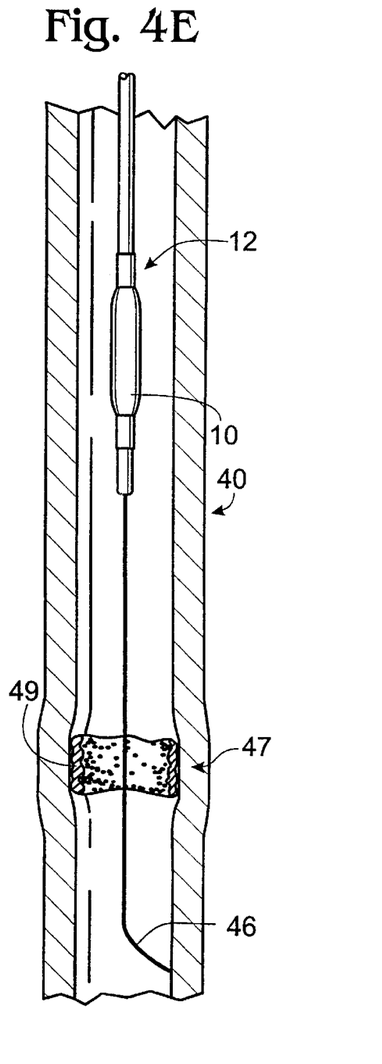
FIG. 4E is a cross-section of the blood vessel and balloon catheter of FIG. 4A with the catheter being withdrawn from the blood vessel.
Figure 5A:
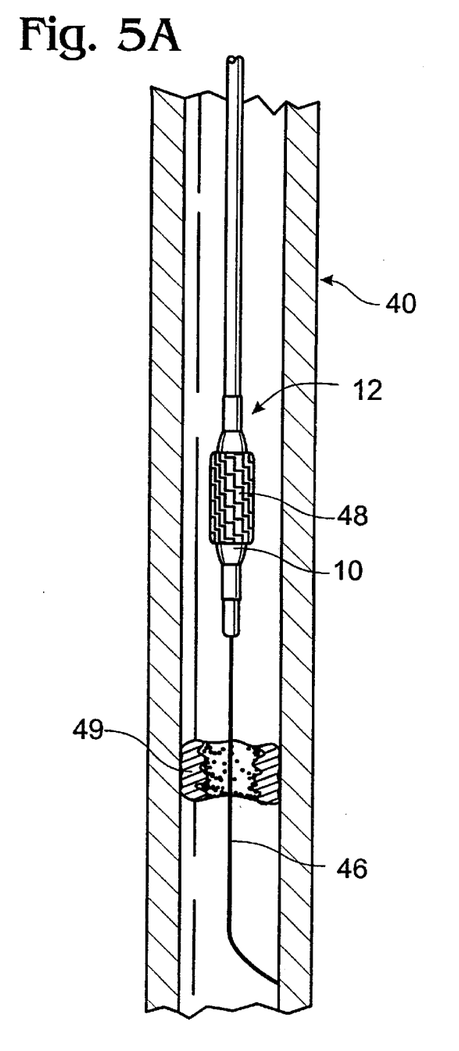
FIG. 5A is a cross-section of a blood vessel and a balloon catheter according to the present invention being fed along a guidewire toward a previously relieved area of stenosis, such as that of FIG. 4C, the balloon catheter having a stent placed on a balloon unit thereof
Figure 5B:
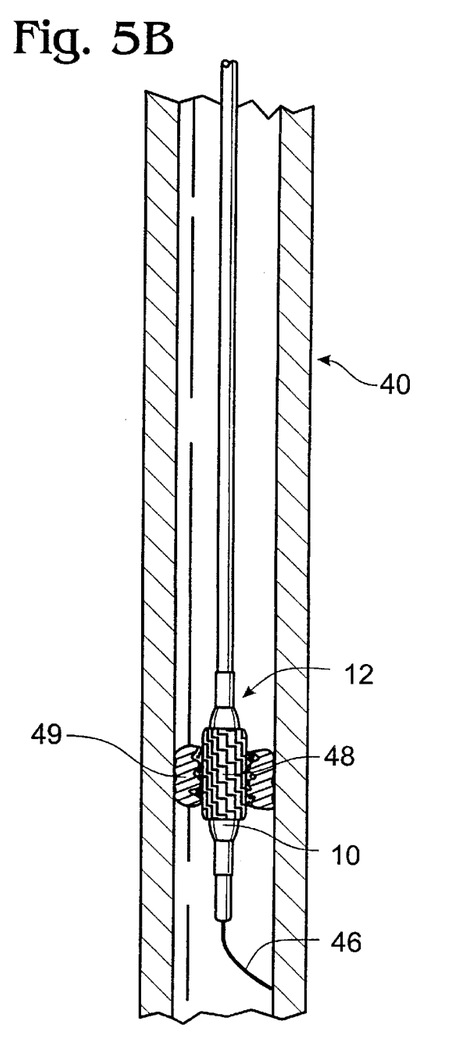
FIG. 5B is a cross-section of the blood vessel and balloon catheter of FIG. 5A with the balloon unit and stent being placed at the area of stenosis.
Figure 5C:
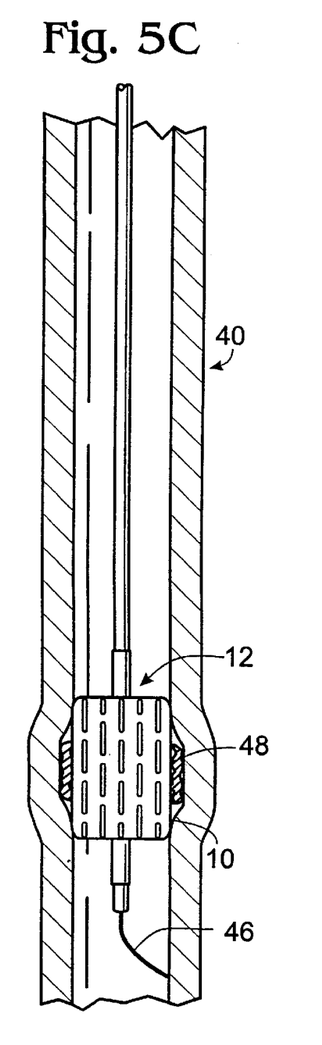
FIG. 5C is a cross-section of the blood vessel and balloon catheter of FIG. 5A with the balloon unit being inflated to expand the stent in place.
Figure 5D:
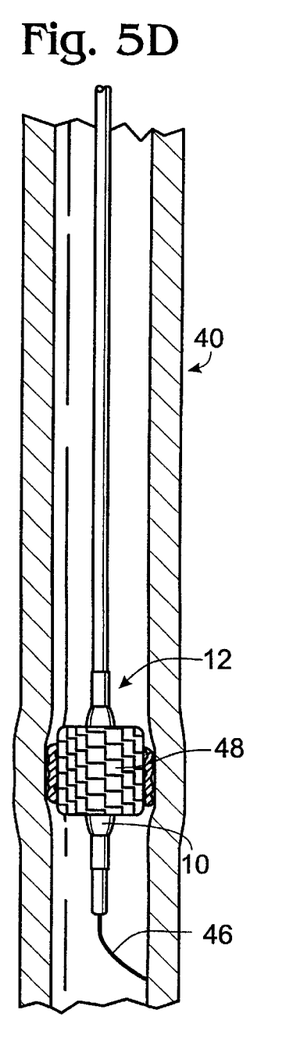
FIG. 5D is a cross-section of the blood vessel and balloon catheter of FIG. 5A with the balloon unit being deflated and the stent being left in place.
Figure 5E:
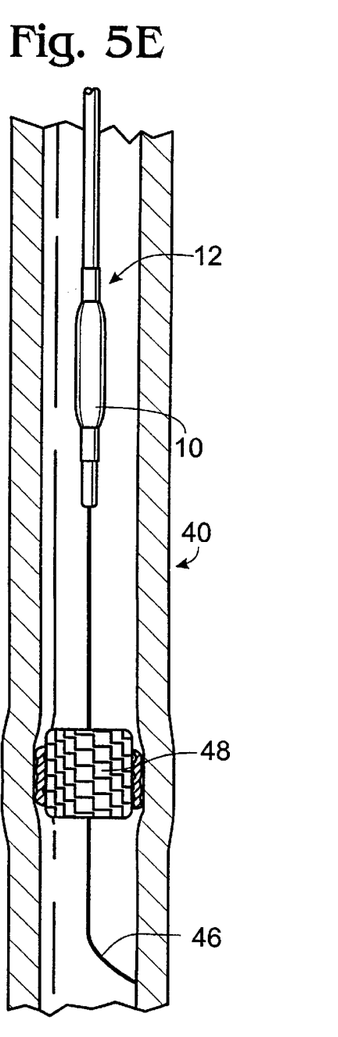
FIG. 5E is a cross-section of the blood vessel and balloon catheter of FIG. 5A with the catheter being withdrawn from the blood vessel.

Referring to FIGS. 1 and 2, a preferred embodiment of a balloon unit 10 for use in a balloon catheter 12 comprises an inner balloon 14 attached at ends 16 and 18 thereof circumferentially around a catheter shaft 20, and a substantially similarly sized outer balloon 22 overlaid substantially on top of the inner balloon 14. Preferably, the catheter shaft is a flexible tube formed of a suitable thermoplastic material, such as polyethylene, polyvinylchloride, polyurethane, nylon or the like, though the tube can be formed of stainless steel or other inert, rigid material. The inner balloon 14 makes a substantially leak-tight seal at the ends 16 and 18 with the shaft 20 and, preferably, with the outer balloon 22.

The catheter 12 is generally adapted for the procedure in which it is to be employed, as will be readily appreciated by those having ordinary skill in the art. For example, a stent placement procedure, described below, requires that the catheter 12 be structurally adapted to withstand a high internal pressurization.

The outer balloon 22 is also attached to the catheter shaft 20 at ends 24 and 26 thereof, so that working portions 30 of the inner balloon 14 and the outer balloon 22 are permitted to move relative to one another, to provide improved surface and structural characteristics in the balloon unit 10. Preferably, the ends 24 and 26 of the outer balloon 22 are disposed substantially over the ends 16 and 18 of the inner balloon 14; however, the outer balloon 22 may be longer or shorter than the inner balloon 14, and may incompletely overlap the inner balloon without departing from the principles of the present invention, it being important only that predetermined working portions 30 of the balloons 14 and 22 overlap. Therefore, a portion of the outer balloon 22 may be bonded either to the inner balloon 14, where the inner balloon extends therebeyond, or to the catheter 12, where the outer balloon extends beyond the inner balloon.

It has been found that best results are achieved in an overlaid balloon catheter wherein the outer balloon 22 comprises a material, such as latex, silicone, or a thermoplastic elastomer, which provides high elasticity and moderate to high surface friction against the body cavity and wherein the inner balloon 14 comprises a relatively thin membrane of flexible, yet strong and relatively inelastic material, such as polyethylene, polyethylene terephthalate, nylon, polyamide, polyvinylchloride, polypropylene or other material known in the art for providing flexibility and strength. Moreover, the strength or other material properties of either balloon may sometimes be adjusted in ways known in the art. For example, the strength of polyethylene may be increased by aligning its polymer chains, thereby increasing its density; a process often referred to as "orientation."

Moderate to high surface friction is desirable in the material of the outer balloon 22 for holding the catheter 12 in place and for better and more complete removal of highly adherent emboli and thrombi. A strong inner balloon 14 supports the outer balloon 22 and reduces the potential for puncture, especially during embolectomy; for breakage resistance of the balloon unit 10 during clot removal from an arterio-venous graft; and for pushing and pulling the balloon unit against atherosclerotic plaques when employed in arteries, or venous valves when employed in the venous system.

The inner balloon 14 includes an outer surface 34 which lies immediately adjacent an inner surface 36 of the outer balloon 22, the two surfaces 34, 36 being permitted to move relative to one another except at the ends 16, 18 and 24, 26. Allowing the two surfaces to move somewhat independently of one another provides for a number of advantages in the present invention. For example, the strong, semi-rigid inner balloon 14 tends to resist complete deflation and tends, upon deflation, to adopt a convoluted, loose configuration of its outer surface 34, somewhat analogous to a folded umbrella. An independently movable, highly elastic outer balloon 22 can provide a superior restoring force in aid of deflating such an inner balloon by overlaying the inner balloon in a configuration that is already taut when the inner balloon is deflated. The always taut outer balloon, then tends to relax to press the inner balloon into a minimum volume of containment. Moreover, the always taut outer balloon can provide an outer surface 38 which is smooth even where the outer surface 34 of the inner balloon is loose and convoluted. A smooth outer surface 38 facilitates insertion of the catheter into and subsequent movement of the catheter through a body cavity, particularly a small blood vessel. Still further, a more highly compressed inner balloon provides for smaller working dimensions of the balloon unit 10, providing for increased facility in small body cavities, such as small blood vessels.

The shaft 20 is provided with at least one inflation lumen 32, the inflation lumen being in fluid communication with the inner balloon 14 via an aperture 23, for inflating the inner balloon by the forced introduction of a fluid, such as air or a saline solution, as understood in the art. Preferably, a remaining space 39 between the inner surface 36 of the outer balloon 22 and the outer surface 34 of the inner balloon 14 is provided with no means for inflation, the remaining space being substantially sealed between the surfaces 34 and 36 and the ends 16, 18, 24 and 26, to permit the outer balloon to provide a back-up seal to the inflation lumen 32. However, this redundancy feature is not a requisite for practice of the present invention. Inflation of the outer balloon 22 is then accomplished by inflating the inner balloon. The remaining space 39 is normally of insubstantial volume, as the surfaces 34 and 36 are preferably in substantial contact with one another.

It is to be recognized that, while a specific overlay dual balloon catheter and method for use thereof has been shown as the preferred embodiment of the invention, other configurations could be utilized, in addition to configurations already mentioned, without departing from the principles of the invention. In particular, it is anticipated that any number of combinations of inner and outer balloon materials may be employed to provide an optimum configuration for different uses. Further, known materials may be processed to optimize their mechanical and chemical properties. Moreover, length, thickness and overlap of the inner and outer balloons can all be varied as needed in a particular application without departing from the principles of the invention. Indeed, it is one of the outstanding advantages of the present invention that a heretofore unmatched number of variations are made available for combining the outstanding features of diverse materials and thereby for tailoring a balloon unit to a particular application in ways heretofore impractical or impossible.

Moreover, multiple lumens within the catheter may be employed without departing from the principles of the present invention, and are often advantageous. For example, multiple lumens may provide for the use of stylets for stiffness, guidewires for catheter placement and irrigation or aspiration.

Four preferred methods for use of the overlay dual balloon catheter will next be described. A first preferred method employs the overlay dual balloon catheter of the present invention in an embolectomy or thrombectomy procedure. Referring to FIGS. 3A–3D, which depict the below-described process in a sequence beginning with FIG. 3A and culminating with FIG. 3D, a vessel 40 is clamped below an obstruction 41 and the catheter 12 employing the aforedescribed balloon unit 10 in a deflated condition is placed into the vessel through an incision 44. The catheter 12 is fed forwardly through the obstruction 41 and the balloon unit 10 is inflated subsequent to its clearing the obstruction. The catheter 12 is then pulled backwardly against the obstruction, pulling the balloon unit 10 and the obstruction back to the site of incision for removal.

The balloon unit 10 of the present invention confers a number of advantages in the thrombectomy and embolectomy procedure. For example, the outer balloon 22 may employ a high surface friction material, such as latex, while the inner balloon 14, may be comprised of a material which confers greater strength to the balloon unit 10. Prior art balloons, typically comprised of latex, employed for thrombectomy and embolectomy are susceptible to breakage, though the stickier surface of a latex outer balloon 14 is better able to seal against the vessel wall and better scour the obstruction. Therefore, the present invention maintains the advantages of employing a latex balloon while overcoming its disadvantages.

A second preferred method employs the overlay dual balloon catheter of the present invention in an angioplasty procedure. Referring to FIGS. 4A–4E, which depict the below-described process in a sequence beginning with FIG. 4A and culminating with FIG. 4E, a guidewire 46 has been placed into the vessel 40 through the incision 44. The guidewire is fed into the vessel incision and advanced beyond the stenotic area. The overlay dual balloon catheter is then fed over the guidewire and positioned at the stenotic area. The catheter 12 for use with the guidewire is typically a dual lumen catheter wherein one of the lumens, for passing the guidewire, has an open distal tip, the other lumen being in fluid communication with the balloon unit to inflate the balloon. The catheter is positioned with the aid of fluoroscopy at the area of a stenosis 47 formed of a stenotic material 49, typically plaque, adhering to the vessel wall, so that the balloon unit 10 contacts the area of stenosis. The balloon unit is then inflated against the stenosis and thereby pressed into the vessel wall. The vessel is thereby opened at the area of stenosis, by compression and partial collapse of the stenotic material 49. The balloon unit 10 is subsequently deflated and the catheter withdrawn from the vessel through the incision. If stent placement is intended, the guidewire 46 is typically left in place in order to guide the catheter 12 therefor, as described below; however, this is not always required.

The balloon unit 10 confers a number of advantages when employed in an angioplasty procedure. Typically, angioplasty balloons are relatively inelastic and, when deflated, have the aforedescribed convolutions and folds. These convolutions and folds make it difficult to insert the balloon through the vessel. The taut outer balloon 22 of the present invention covers the convolutions and folds of a relatively inelastic but strong inner balloon 14, making the balloon unit 10 easier to insert.

A third preferred method employs the overlay dual balloon catheter of the present invention for stent placement, usually following an angioplasty procedure. Referring to FIGS. 5A–5E, which depict the below-described process in a sequence beginning with FIG. 5A and culminating with FIG. 5E, the catheter 12 is fed over the guidewire 46, through the incision 44 and the vessel 40. In this case, a dual lumen catheter is also used. A stent 48 is placed over the balloon unit 10 and a crimping device is used to compress the stent in position thereover. The position of the catheter is monitored typically by either X-ray or fluoroscopy and a proper position of the balloon unit 10 is confirmed thereby. The balloon unit 10 is then inflated to expand the stent in place. The balloon unit 10 is then deflated and the catheter 12 withdrawn from the vessel 40 through the incision 44.

The balloon unit 10 confers a number of advantages when employed in a stent placement procedure. For example, the compressible surface on the outer balloon 22 helps to hold the stent in place during insertion, while a strong inner balloon 14 permits expansion thereof A fourth preferred method employs the overlay dual balloon catheter of the present invention for vessel or duct occlusion. The catheter 12 is inserted into a vessel or duct and passed with or without a guidewire as needed, to a site therein to be occluded. Occlusion may be for prevention of blood flow during a surgical procedure as well as for control of movement of irrigation fluids, radiopaque dyes and for aspiration and removal of fluids, ductal debris and stones.

The balloon unit 10 confers a number of advantages when employed for vessel or duct occlusion. For example, aortic occlusion requires retention of a catheter balloon against very high blood pressure and flow. The balloon unit 10 according to the present invention provides a capability to inflate to high pressures without breaking, and employs a coefficient of friction so as to resist being dislodged by high blood flow and pressure, both contributing to holding the balloon unit in place. Moreover, sharp calcified arterial plaque may puncture a catheter balloon, while the balloon unit 10 according to the present invention has an increased puncture resistance.

The terms and expressions which have been employed in the foregoing specification are used therein as terms of description and not of limitation, and there is no intention of the use of such terms and expressions of excluding equivalents of the features shown and described or portions thereof, it being recognized that the scope of the invention is defined and limited only by the claims which follow.

I claim:

1. A balloon catheter, comprising:

a catheter having a lumen therein;

an inner balloon disposed around a portion of said catheter, said inner balloon having an outer surface and said catheter having an aperture therein for fluid communication between said lumen and said inner balloon, for inflating said inner balloon; and an outer balloon having an inner surface, said outer balloon being disposed over said inner balloon so that said inner surface of said outer balloon and said outer surface of said inner balloon remain substantially in contact with, and are movable relative to, one another during said inflating.

2. The catheter of claim 1, wherein said outer surface of said inner balloon and said inner surface of said outer balloon lie substantially coextensively in contact with one another.

3. The catheter of claim 1, wherein said inner balloon is attached at opposing ends circumferentially around said catheter so as to form respective fluid-tight seals.

4. The catheter of claim 3, wherein said outer balloon is attached at opposing ends circumferentially around said catheter so as to form respective fluid-tight seals.

5. The catheter of claim 4, wherein said outer balloon is attached to opposing ends around said respective opposing ends of said inner balloon.

6. The catheter of claim 1, wherein the elasticity of said outer balloon is higher than the elasticity of said inner balloon.

7. The catheter of claim 6, wherein the tensile strength of said inner balloon is greater than the tensile strength of said outer balloon.

8. The catheter of claim 7, wherein said outer balloon provides higher surface friction than said inner balloon.

9. The catheter of claim 1, wherein the tensile strength of said inner balloon is greater than the tensile strength of said outer balloon.

10. The catheter of claim 1, wherein said outer balloon provides higher surface friction than said inner balloon.

11. The catheter of claim 1, wherein, in an uninflated state, said outer balloon is under a predetermined amount of tension relative to said inner balloon.

12. The catheter of claim 1, wherein said inner balloon comprises a polyethylene.

13. The catheter of claim 1, wherein said inner balloon comprises polyethylene terephthalate.

14. The catheter of claim 1, wherein said inner balloon comprises a nylon.

15. The catheter of claim 1, wherein said inner balloon comprises a polyamide.

16. The catheter of claim 1, wherein said inner balloon comprises a polyvinylchloride.

17. The catheter of claim 1, wherein said outer balloon comprises a latex.

18. The catheter of claim 1, wherein said outer balloon comprises a silicone.

19. The catheter of claim 1, wherein said outer balloon comprises a thermoplastic elastomer.

20. The catheter of claim 1, wherein the space between said outer surface of said inner balloon and said inner surface of said outer balloon is substantially sealed from fluid communication with space outside of said outer balloon.

21. The catheter of claim 20, wherein the space between said outer surface of said inner balloon and said inner surface of said outer balloon is substantially sealed from fluid communication with space inside said inside balloon.

22. A balloon catheter, comprising:

a catheter having a lumen therein;

an inner balloon disposed around a portion of said catheter, said catheter having an aperture therein for fluid communication between said lumen and said inner balloon; and an outer balloon disposed over said inner balloon, wherein in an uninflated state of said inner balloon, said outer balloon is under a predetermined amount of tension relative to said inner balloon.

23. The catheter of claim 22, wherein said inner balloon has an outer surface and said outer balloon has an inner surface, and wherein said outer surface of said inner balloon and said inner surface of said outer balloon are movable relative to one another while remaining substantially in contact with one another.

24. The catheter of claim 22, wherein said inner balloon is attached at opposing ends circumferentially around said catheter so as to form respective fluid-tight seals.

25. The catheter of claim 24, wherein said outer balloon is attached at opposing ends circumferentially around said catheter so as to form respective fluid-tight seals.

26. The catheter of claim 25, wherein said outer balloon is attached to opposing ends around said respective opposing ends of said inner balloon.

27. The catheter of claim 22, wherein the elasticity of said outer balloon is greater than the elasticity of said inner balloon.

28. The catheter of claim 22, wherein the tensile strength of said inner balloon is greater than the tensile strength of said outer balloon.

29. The catheter of claim 22, wherein said outer balloon provides higher surface friction than said inner balloon.

* * * * *